(12) United States Patent
Cho et al.

(10) Patent No.: US 7,166,856 B2
(45) Date of Patent: Jan. 23, 2007

(54) APPARATUS AND METHOD TO INSPECT DISPLAY PANELS

(75) Inventors: Sue Jin Cho, Yongin-Si (KR); Hyung Sun You, Suwon-Si (KR); Jang Hee Lee, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 10/938,644

(22) Filed: Sep. 13, 2004

(65) Prior Publication Data

US 2005/0167620 A1    Aug. 4, 2005

(30) Foreign Application Priority Data

Jan. 30, 2004 (KR) .................. 10-2004-0006132

(51) Int. Cl.
*G01N 21/88* (2006.01)
*G01V 8/00* (2006.01)

(52) U.S. Cl. .............. 250/559.45; 250/559.4; 250/559.46; 250/559.07; 250/559.08; 349/192; 356/237.1; 356/390; 382/141

(58) Field of Classification Search ........... 250/559.45, 250/559.46, 559.4, 559.07, 559.08; 356/237.1, 356/237.2, 388, 390; 345/207; 349/192, 349/54, 55; 382/141, 145, 149
See application file for complete search history.

(56) References Cited

U.S. PATENT DOCUMENTS

| 5,771,068 | A  | * | 6/1998  | Sali et al. ..................... 348/92 |
| 6,177,682 | B1 |   | 1/2001  | Bartulovic et al. |
| 6,665,065 | B1 | * | 12/2003 | Phan et al. .............. 356/237.1 |
| 6,867,424 | B2 | * | 3/2005  | Kurosawa et al. ....... 250/559.4 |
| 2002/0085198 | A1 |   | 7/2002  | Sohn |
| 2003/0094586 | A1 | * | 5/2003  | Kurosawa et al. ....... 250/559.4 |
| 2003/0215129 | A1 | * | 11/2003 | Yang et al. ................ 382/149 |
| 2005/0035311 | A1 | * | 2/2005  | Asakawa et al. ...... 250/559.16 |

* cited by examiner

*Primary Examiner*—Stephone B. Allen
*Assistant Examiner*—Davienne Monbleau
(74) *Attorney, Agent, or Firm*—Stanzione & Kim, LLP

(57) ABSTRACT

An apparatus and method to inspect a display panel that can correctly detect a defect of the display panel itself. In the method of inspecting the display panel, a first image is captured from the display panel in a state in which no pattern is applied to the display panel. Light is then irradiated on the display panel in a state in which a pattern is applied to the display panel, and a second image is captured from the display panel. The first image can be compared with the second image, and a determination can be made as to whether or not a defect of the display panel is present.

22 Claims, 7 Drawing Sheets

APPARATUS AND METHOD TO INSPECT DISPLAY PANELS

CROSS-REFERENCE TO RELATED APPLICATIONS

This application claims the benefit of Korean Patent Application No. 2004-6132, filed Jan. 30, 2004, in the Korean Intellectual Property Office, the disclosure of which is incorporated herein by reference.

BACKGROUND OF THE INVENTION

1. Field of the Invention

The present general inventive concept relates to an apparatus and method to inspect display panels, and more particularly, to an apparatus and method to inspect display panels to correctly detect a defect of the display panel itself.

2. Description of the Related Art

Generally, a display panel serves as a display unit for visually displaying data and includes a liquid crystal display (LCD) panel, a plasma display panel (PDP), etc.

The LCD panel is a display unit employing electro-optic properties of the liquid crystals having an intermediate characteristic between a liquid and a solid. That is, the LCD panel controls an amount of light generated from a backlight by moving internal liquid crystals and displays a specific pattern on a screen.

Because a desired pattern may be not appropriately generated due to an external substance or an electric defect of the panel itself in a process for manufacturing the LCD panel, various inspection devices are being developed to detect a defect of the LCD panel.

A conventional inspection device for use in the LCD panel includes a typical backlight, a pattern generator for applying a preset pattern to the LCD panel so that an inspection operation can be performed, a camera for picking up the LCD panel to capture an image of the LCD panel, and a microcomputer for controlling an overall operation of the inspection device.

As described above, the conventional inspection device for use in the LCD panel applies a test pattern to the LCD panel to be inspected so that a defect of the LCD panel can be detected, and then turns on the backlight. Then, the camera picks up the LCD panel so that the image of the LCD panel can be captured. When the image of the LCD panel has been captured, the microcomputer analyzes the captured image and determines whether or not the LCD panel is defective. Types of defects detected by the inspection operation for the LCD panel can be a HIGH defect, an OFF defect, etc. A black color must be entirely displayed when a black pattern is applied to the LCD panel, but light may come out of at least one point of the LCD panel. This case is referred to as the HIGH defect. On the other hand, some region of the LCD panel becoming dark without emitting light may be present when a white pattern is applied to the LCD panel. This case is referred to as the OFF defect.

In addition to a defect of the LCD panel itself when the LCD panel is inspected, the LCD panel can be shown as if it is defective due to an external factor. That is, when the backlight is turned on to inspect the LCD panel, a surface scratch, dust, etc., on a protection film attached to protect the LCD panel in the manufacturing process can cause light transmitted from the LCD panel to be dispersed. In this case, the image captured by picking up the LCD panel displays a defect point due to the dust or surface scratch in the same form as a form in which the LCD panel itself is defective.

Because the conventional apparatus and method for inspecting the LCD panel cannot discriminate a defect of the LCD panel itself from a defect due to a surface scratch or dust, there is a problem in that the LCD panel can be erroneously inspected.

SUMMARY OF THE INVENTION

Therefore, the present general inventive concept has been made in view of the above and/or other problems, and it is an aspect of the present general inventive concept to provide an apparatus and method to inspect display panels to correctly detect a defect of the display panel itself.

Additional aspects and advantages of the present general inventive concept will be set forth in part in the description which follows and, in part, will be obvious from the description, or may be learned by practice of the general inventive concept.

The foregoing and/or other aspects of the present general inventive concept are achieved by providing a method of inspecting a display panel, the method including capturing a first image of the display panel in a state in which no pattern is applied to the display panel, irradiating light on the display panel in a state in which a pattern is applied to the display panel, and capturing a second image of the display panel, and comparing the first image with the second image and determining whether a defect of the display panel is present.

The foregoing and/or other aspects of the present general inventive concept are also achieved by providing a method of inspecting a display panel with a protection film, the method including irradiating light on the protection film and capturing a first image of the protective film, irradiating light on the display panel in a state in which a pattern is applied to the display panel, capturing a second image of the protective film, and comparing the first image with the second image to determine whether a defect of the display panel is present.

The foregoing and/or other aspects of the present general inventive concept are also achieved by providing an apparatus to inspect a display panel, including a first light unit to irradiate light on a surface of the display panel, a second light unit to irradiate light on a back surface of the display panel, a pickup unit to capture a first image of the display panel in a state in which the pickup unit is coupled to the first light unit, and to capture a second image of the display panel in a state in which the pickup unit is coupled to the second light unit, and a controller to receive the first and second images from the pickup unit, to compare the first image with the second image, and to determine whether or not a defect of the display panel is present.

The foregoing and/or other aspects of the present general inventive concept are also achieved by providing an apparatus to inspect a display panel with a protection film, including a first light unit to irradiate light to on the protection film, a second light unit to irradiate light to on a back surface of the display panel, a pickup unit to capture a first image of the protection film in a state in which the pickup unit is coupled to the first light unit, and to capture a second image from the display panel and the protective film, and a controller to receive the first and second images from the pickup unit, to compare the first image with the second image, and to determine whether or not a defect of the display panel is present.

BRIEF DESCRIPTION OF THE DRAWINGS

These and/or other aspects and advantages of the present general inventive concept will become apparent and more readily appreciated from the following description of the embodiments, taken in conjunction with the accompanying drawings of which.

DETAILED DESCRIPTION OF THE PREFERRED EMBODIMENTS

Figure 1:
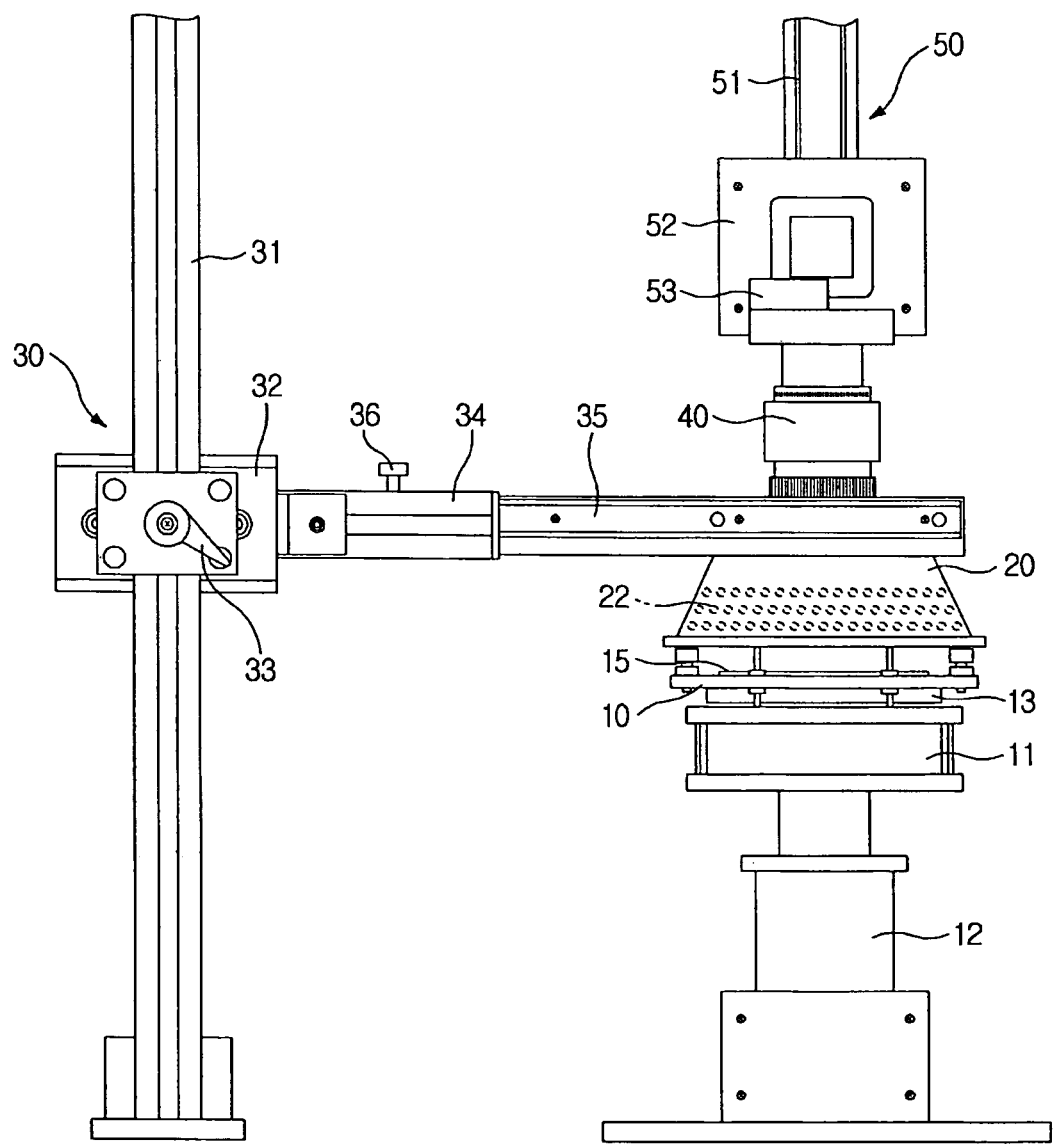
FIG. 1 is a front view illustrating an apparatus to inspect a display panel in accordance with an embodiment of the present general inventive concept.

Reference will now be made in detail to the embodiments of the present general inventive concept, examples of which are illustrated in the accompanying drawings, wherein like reference numerals refer to the like elements throughout. The embodiments are described below in order to explain the present general inventive concept by referring to the figures.

Referring to FIG. 1, an apparatus to inspect a display panel in accordance with an embodiment of the present general inventive concept can include a stage 10 to position a liquid crystal display (LCD) panel 15 to be inspected, a light unit 20 supported by a light support 30 to irradiate light on the LCD panel 15 at a top portion of the LCD panel 15, and a high magnification camera 40 installed on a camera support 50 to capture an image of the LCD panel 15 at a front portion of the light unit 20.

The light support 30 includes a first elevating rail 31 arranged in a vertical direction, a first elevating member 32 coupled to the first elevating rail 31 to enable a vertical moving operation, and a fixing lever 33 installed on the first elevating member 32 to fix the first elevating member 32. A horizontal moving rail 34 can be provided at a side of the first elevating member 32, and a horizontal moving slider 35 to enable a horizontal moving operation can be installed on the horizontal moving rail 34. A lower surface of the horizontal moving slider 35 can be coupled to an upper surface of the light unit 20. The apparatus to inspect the display panel can adjust a horizontal position by moving the horizontal moving slider 35. A second fixing lever 36 to fix the horizontal moving rail 34 can be provided on an upper surface of the horizontal moving rail 34.

A camera support 50 can include a second elevating rail 51 and a second elevating member 52 coupled to the second elevating rail 51 to enable a vertical moving operation. The high magnification camera 40 can be attached in front of the second elevating member 52 by a bracket 53, and hence a vertical position of the high magnification camera 40 can be adjusted when the second elevating member 52 is shifted.

A backlight 11 can be installed at a lower portion of the stage 10 to irradiate light to the LCD panel 15. The backlight 11 can be supported by a backlight support 12. Here, it is an aspect of the general inventive concept that the stage 10 is made of a material that can transmit light irradiated at the bottom portion thereof from the backlight 11 to a front portion thereof. A probing unit 13 to apply, to the LCD panel 15, a pattern signal sent from a pattern generator (denoted by a reference numeral 63 shown in FIG. 2), to be described below, can be arranged between the stage 10 and the backlight 11.

Figure 2:
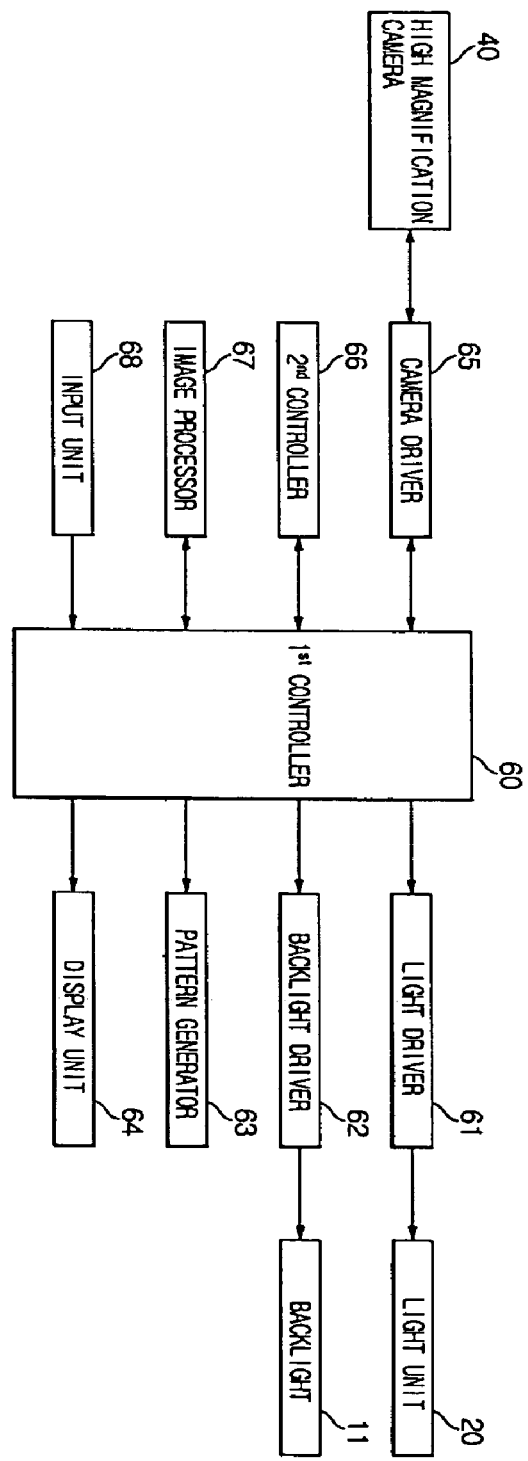
FIG. 2 is a block diagram illustrating a configuration of the apparatus to inspect a display panel in accordance with FIG. 1.

As shown in FIG. 2, an apparatus to inspect the display panel in accordance with an embodiment of the general inventive concept can further include a camera driver 65 to drive the high magnification camera 40, a light driver 61 to drive the light unit 20, a backlight driver 62 to drive the backlight 11, and a pattern generator 63 to generate a pattern signal to be applied to the LCD panel 15.

The apparatus to inspect the display panel in accordance with FIGS. 1 and 2 can further include an image processor 67 to process image signals sent from the high magnification camera 40 and to recover a plurality of images from the processed image signals, and a second controller 66 to compare the images based on the image signals processed by the image processor 67, and to determine the presence of a defect of the LCD panel 15 itself. For this, the image processor 67 can store data necessary to recover the images from the image signals in advance. The plurality of images captured from the LCD panel 15 can be divided into a number of cells by the second controller 66, respectively. Furthermore, the second controller 66 can compare specific image cells corresponding to the same point in the plurality of images and determines whether or not the specific image cells match according to a result of the comparison.

Moreover, the apparatus to inspect the display panel in accordance with FIG. 2 includes a display unit 64 to display an image recovered by the image processor 67, an input unit 68 to input a control command, and a first controller 60 to control an overall operation of the inspection apparatus.

A method of inspecting a display panel using the apparatus of FIGS. 1 and 2, in accordance with another embodiment of the general inventive concept will be described with reference to FIGS. 3 to 5. The display panel 15 to be inspected by the method of this embodiment includes a protection film 18 to protect the LCD panel 15 attached to a surface thereof in a manufacturing process.

Figure 3:
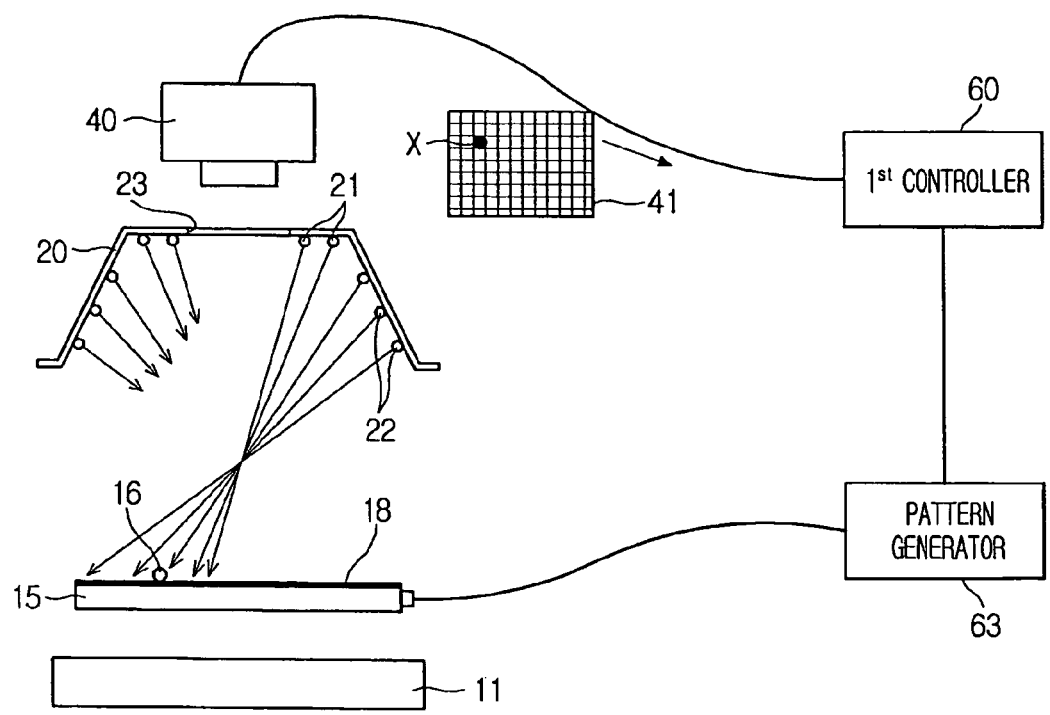
FIG. 3 is an explanatory view illustrating a process to capture a first image by use of the apparatus shown in FIGS. 1 and 2 in accordance with another embodiment of the present general inventive concept.

The light unit 20 included in the apparatus to inspect the display panel in accordance with FIGS. 1 and 2 can include top light elements 21 installed on a top surface inside the light unit 20 and inclined light elements 22 installed on inclined surfaces inside the light unit 20, as shown in FIG. 3. The top light elements 21 can include a plurality of light emitting devices, such as a plurality of lamps or light emitting diodes (LEDs), etc., that can be arranged at equivalent intervals in the form of a ring. The inclined light elements 22 can include a plurality of light emitting devices, such as a plurality of lamps or LEDs, etc., that can be arranged at equivalent intervals in the form of multiple rings. When the light emitting devices are turned on, as the plurality of light emitting devices are regularly arranged at different positions, light reaching the LCD panel 15 may have various irradiation angles. A pickup aperture 23 can be formed in the top portion of the light unit 20 so that the high magnification camera 40 can pick up the LCD panel 15. A form and installation position of the light unit 20 can be variously changed. For example, the light emitting devices can be installed below the LCD panel 15 so that they can irradiate light in an upward direction, and the irradiated light can be reflected by a reflection plate installed at the top portion of the LCD panel 15 so that the reflected light can be transferred to the LCD panel 15.

Figure 5:
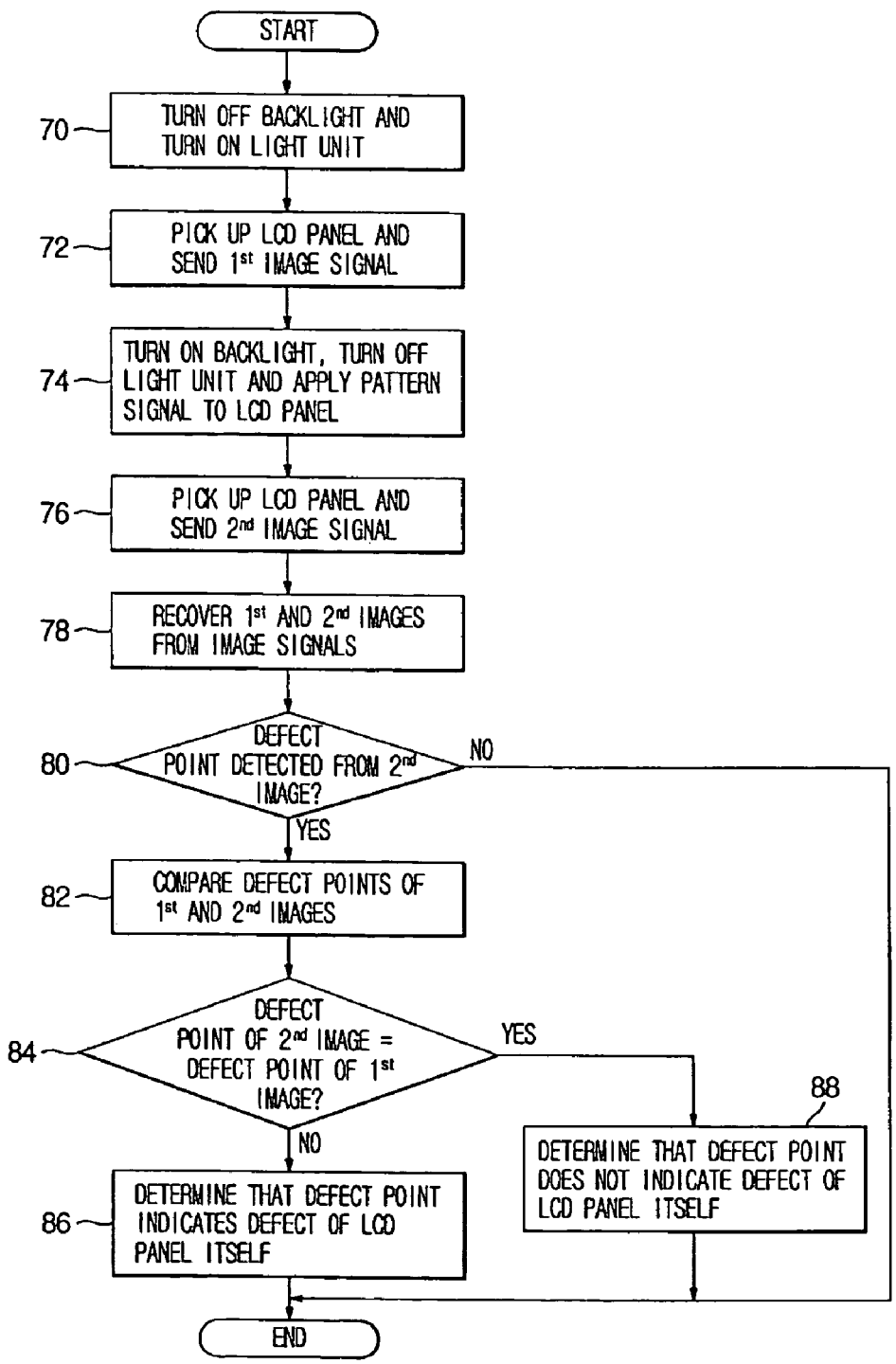
FIG. 5 is a flow chart illustrating a method of inspecting a display panel in accordance with another embodiment of the present general inventive concept.

As shown in FIGS. 3 and 5, and referring to FIG. 2, the controller 60 can send control signals to the light driver 61 and the backlight driver 62 so that the light unit 20 can be turned on and the backlight 11 can be turned off, at operation 70. At this point, no pattern is applied to the LCD panel 15. In FIG. 3, reference numeral 16 denotes dust attached to the protection film 18. As the backlight 11 is turned off, the LCD panel darkens. The dust 16 attached to the surface of the protection film 18 or a surface scratch (not shown) shines brightly by light irradiated at various angles shown in FIG. 3. In this state, an image 41 captured from the LCD panel 15 by using the high magnification camera 40 can contain a point X of the dust 16 or surface scratch displayed in the same form as in the case of a defect of the LCD panel 15 itself. The image 41 captured by the high magnification camera 40 can be converted into a first image signal, and then the first image signal can be sent to the controller 60, at operation 72.

Figure 4:
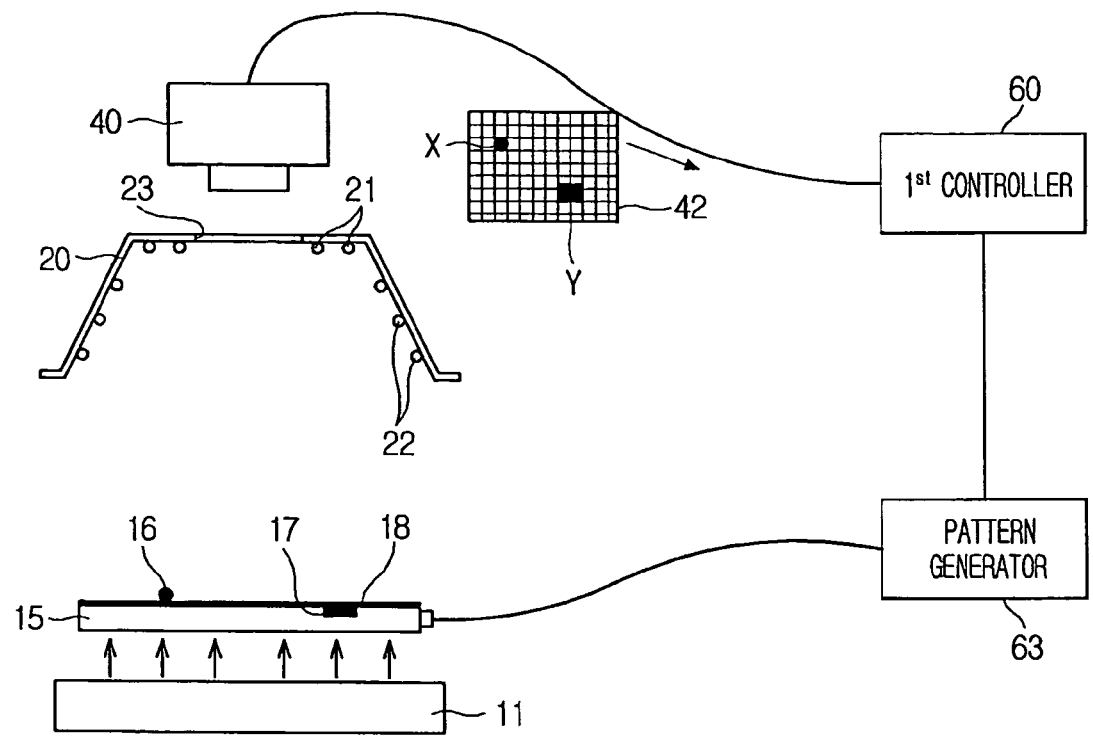
FIG. 4 is an explanatory view illustrating a process to capture a second image by use of the apparatus shown in FIGS. 1 and 2 in accordance with another embodiment of the present general inventive concept.

As shown in FIGS. 4 and 5, the controller 60 can send control signals to the light driver 61 and the backlight driver 62 so that the backlight 11 can be turned on and the light unit 20 can be turned off, at operation 74. Furthermore, the controller 60 can send a control signal to the pattern generator 63 so that a pattern (e.g., a black pattern) can be applied to the LCD panel 15. In FIG. 4, reference numeral 17 denotes a defect of the LCD panel itself, such the surface scratch. When the pattern has been applied to the LCD panel 15 and the backlight 11 has been turned on, the LCD panel displays a preset pattern. However, the preset pattern will not be formed at a defect point Y, thus indicating the defect of the LCD panel 15 itself, and the dust 16 or the surface scratch 17 will disperse light going through the LCD panel 15. In this state, the controller 60 enables the high magnification camera 40 to capture an image 42 from the LCD panel 15. The captured image 42 can display both the point Y indicating the defect of the LCD panel 15 itself and the point X indicating the presence of the dust 16 or surface scratch. The captured image 42 can then be converted into a second image signal and then the second image signal is sent to the controller 60, at operation 76.

When the first and second image signals are sent to the controller 60, the first controller 60 enables the image processor 67 to recover the first and second images 41 and 42 from the first and second image signals, at operation 78. If the image processor 67 has completed the recovery operation, the first and second images 41 and 42 can be sent to the second controller 66. Upon receiving the first and second images 41 and 42, the second controller 66 can determine whether a defect point is present in the second image 42, at operation 80. The defect point of the second image 42 can be detected by determining whether the second image 42 matches an image of the preset pattern. When it is determined that no defect of the LCD panel 15 itself is present (if no defect point is present in the second image 42), a process cycle can be terminated. On the other hand, if it is determined that a defect point is present in the second image 42, the second controller 66 can divide each of the first and second images 41 and 42 into a plurality of cells to compare the image cells of the first and second images 41 and 42, at operation 82, and can determine whether the defect point of the second image 42 matches that of the first image 41, at operation 84.

When the defect point displayed on the second image 42 is also displayed on the first image 41, if the defect point of the second image 42 matches that of the first image 41, it is determined that the LCD panel 15 itself is not defective. Moreover, it is determined that the defect point of each of the first and second images 41 and 42 has resulted from dust 16 or a surface scratch on the protection film 18, at operation 88. In this embodiment, it can be determined that a defect detected from a point X of each of the first and second images 41 and 42 does not indicate a defect of the LCD panel 15 itself. However, if the defect point of the second image 42 does not match that of the first image 41, a defect indicated in the second image 42 is determined to be a defect of the LCD panel 15 itself, at operation 86. Because a point of a defect can be detected from an image divided into a plurality of cells, a point (or pixel) of the defect incurred in the LCD panel 15 can be identified. Furthermore, in this embodiment, when a point Y indicating a defect point in the second image 42 is not displayed on the first image 41, the point Y can be determined to be a defect point of the LCD panel 15 itself.

A method of inspecting a display panel in accordance with another embodiment of the present general inventive concept will be described with reference to FIGS. 6 and 7, while referring back to FIG. 2.

Figure 6:
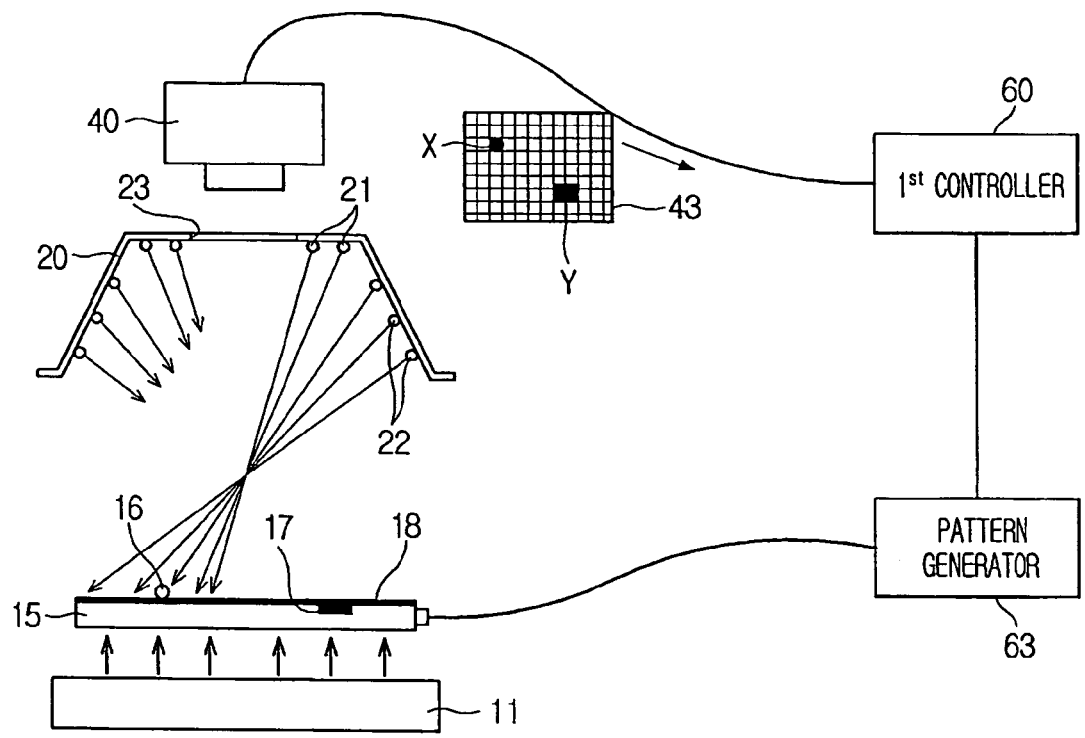
FIG. 6 is an explanatory view illustrating a process to capture a first temporal image by use of the apparatus shown in FIGS. 1 and 2 in accordance with another embodiment of the present general inventive concept.
Figure 7:
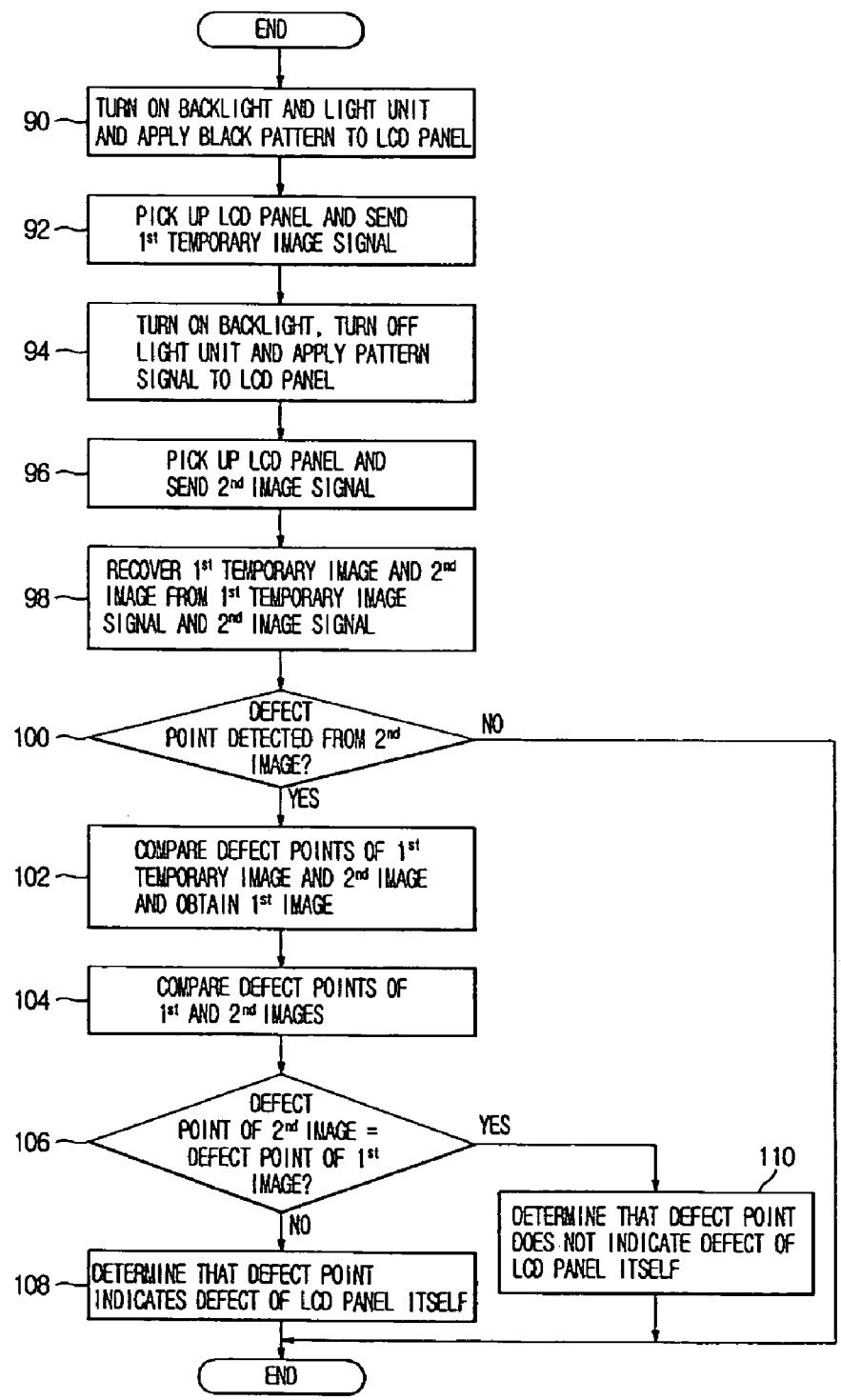
FIG. 7 is a flow chart illustrating a method of inspecting a display panel in accordance with another embodiment of the present general inventive concept.

As shown in FIGS. 6 and 7, the controller 60 (FIG. 2) can send control signals to the light driver 61 and the backlight driver 62 so that the light unit 20 can be turned on and the backlight 11 can be turned on, at operation 90. A black pattern can be applied to the LCD panel 15 so that a background of the LCD panel 15 becomes black. In FIG. 6, reference numeral 16 denotes dust attached to the protection film 18, and reference numeral 17 denotes a defect of the LCD panel 15 itself. In a state in which the backlight 11 is turned on and the black pattern is applied to the LCD panel 15, the LCD panel 15 darkens. The dust 16 attached to the surface of the protection film 18 or a surface scratch (not shown) brightly shines by light irradiated at the various angles, as shown in FIG. 6. In this state, the controller 60 enables the high magnification camera 40 to capture an image 43 from the LCD panel 15. The captured image 43 is illustrated as displaying both the point X of a dust 16 (or a surface scratch) and a defect point Y of the LCD panel 15 itself. The image 43, captured by the high magnification camera 40, can be converted into a first temporary image signal, and then the first temporary image signal can be sent to the controller 60.

Referring to FIG. 7, operations 94 to 96 to acquire a second image signal can be applied to this embodiment as was described in the previous embodiment.

When the first temporary image signal and the second image signal are sent to the controller 60, the first controller 60 can enable the image processor 67 to recover the first temporary image 43 and a second image 42 from the first temporary image signal and the second image signal, respectively, at operation 98. If the image processor 67 has completed the recovery operation, the first temporary image 43 and the second image 42 can be sent to the second controller 66. Upon receiving the first temporary image 43 and the second image 42, the second controller 66 can determine whether a defect point is present in the second image 42, at operation 100. The presence of the defect point in the second image 42 can be determined by determining whether or not the second image 42 matches an image of the preset pattern. When it is determined that no defect of the LCD panel 15 itself is present (if no defect point is present in the second image 42), a process cycle is terminated. On the other hand, if it is determined that a defect point is present in the second image 42, the second controller 66 can compare the first temporary image 43 and the second image 42, and then obtain a first image 41, at operation 102. In order for the first image 41 to be obtained, the second controller 66 can divide each of the first temporary image 43 and the second image 42 into a plurality of cells. The second controller 66 can compare image cells of the first temporary image 43 and the second image 42 located at the same point. Because all of the first temporary image 43 and the second image 42 have been captured in a state in which the patterns have been applied, the defect point Y of the LCD panel 15 itself will be displayed on the first temporary image 43 and the second image 42 in a substantially equal form or brightness.

However, the point X in which the dust 16 or surface scratch is present is brighter in the captured first temporary image 43 in the state in which the light unit 20 is turned on, in comparison with the captured second image 42 in the state in which the light unit 20 is turned off. Thus, the first temporary image 43 and the second image 42 are displayed as if the defect point is present in both of the images 43 and 42, but a defect point based on a brightness difference between the first temporary image 43 and the second image 42 is determined to be a point in which the dust 16 or the surface scratch is present. As a result, it can be found that the defect point based on the brightness difference does not indicate a defect of the LCD panel 15 itself.

The second controller 66 can maintain the defect point based on the brightness difference between the first temporary image 43 and the second image 42, and can remove a defect point without a brightness or form difference, thereby acquiring the first image 41. As a result, the first image 41 displays only the defect point in which the dust 16 or surface scratch is present.

If the first image 41 has been acquired, the second controller 66 can divide each of the first and second images 41 and 42 into a plurality of cells and can compare the image cells of the first and second images 41 and 42, at operation 104, and then can determine whether or not a defect point of the second image 42 matches that of the first image 41, at operation 106.

A defect point displayed on the second image 42 can also be displayed on the first image 41 if the defect point of the first image 41 matches that of the second image 42, and hence it can be determined that the defect point displayed on each of the first and second images 41 and 42 does not indicate a defect of the LCD panel 15 itself, but indicates a defect caused by the dust 16 or surface scratch on the protection film 18, at operation 110. In this embodiment, a defect point X can be detected from the first and second images 41 and 42, and it can be determined that the detected defect point X does not indicate a defect of the LCD panel 15 itself.

On the other hand, if a defect point of the second image 42 does not match that of the first image 41, it is determined that the defect point displayed on the second image 42 indicates a defect of the LCD panel 15 itself, at operation 108. When a point of the defect can be identified from the image divided into a plurality of cells, a defect point (or pixel) of the LCD panel 15 can be identified. In this embodiment, when the defect point Y of the second image 42 is not displayed on the first image 41, the defect point Y can be determined to be a defect point of the LCD panel 15 itself.

As apparent from the above description, the present general inventive concept provides an apparatus and method to inspect a display panel that can correctly detect a defect of the display panel itself, and that can prevent an erroneous decision when the display panel is inspected.

Although a few embodiments of the present general inventive concept have been shown and described, it will be appreciated by those skilled in the art that changes may be made in these embodiments without departing from the principles and spirit of the invention, the scope of which is defined in the appended claims and their equivalents.

What is claimed is:

1. A method of inspecting a display panel, comprising:
   capturing a first image of the display panel in a state in which no pattern is applied to the display panel;
   irradiating light on the display panel in a state in which a pattern is applied to the display panel, and capturing a second image of the display panel; and
   comparing the first image with the second image to determine whether or not a defect of the display panel is present.

2. The method according to claim 1, wherein the comparing the first image and second image operation comprises:
   identifying a defect point from each of the first and second images;
   when the defect point is identified from the second image, comparing defect points of the first and second images; and
   when the defect point of the first image is different from that of the second image, determining the identified defect point to be a defect point of the display panel itself.

3. The method according to claim 2, wherein a determination is made that no defect is present in the display panel when no defect point is identified from the second image.

4. The method according to claim 2, wherein a determination is made that the identified defect point is not a defect point of the display panel itself when the defect point of the first image matches that of the second image.

5. The method according to claim 1, wherein the first image is captured by picking up the display panel without applying the pattern to the display panel in a state in which a light unit irradiating light to a surface of the display panel is turned on and a backlight irradiating light to a back surface of the display panel is turned off.

6. The method according to claim 1, wherein the first image is captured by picking up the display panel by applying a black pattern to the display panel in a state in which a light unit irradiating light to a surface of the display panel is turned on and a backlight irradiating light to a back surface of the display panel is turned off.

7. The method according to claim 1, wherein the second image is captured by picking up the display panel in a state in which a light unit irradiating light to a surface of the display panel is turned off and a backlight irradiating light to a back surface of the display panel is turned on.

8. The method according to claim 1, wherein the display panel is a liquid crystal display (LCD) panel.

9. A method for inspecting a display panel with a protection film, comprising the steps of:
   irradiating light to the protection film and picking up the protection film to capture a first image;

irradiating light to the display panel in a state in which a pattern is applied to the display panel, and picking up the pattern and the protection film to capture a second image; and comparing the first image with the second image and determining whether or not a defect of the display panel is present.

10. An apparatus to inspect a display panel, comprising:
a first light unit to irradiate light to a surface of the display panel;
a second light unit to irradiate light to a back surface of the display panel;
a pickup unit to capture a first image of the display panel in a state in which the pickup unit is coupled to the first light unit, and to capture a second image in a state in which the pickup unit is coupled to the second light unit; and
a controller to receive the first and second images from the pickup unit, to compare the first image with the second image, and to determine whether a defect of the display panel is present.

11. The apparatus according to claim 10, wherein the presence of the defect is determined by determining whether a defect point identified from the first image matches that identified from the second image.

12. The apparatus according to claim 10, wherein the first light unit internally comprises a plurality of lamps or light emitting diodes (LEDs) arranged at various positions so that various irradiation angles can be formed.

13. The apparatus according to claim 10, wherein the display panel is a liquid crystal display (LCD) panel.

14. An apparatus to inspect a display panel with a protection film, comprising:
a first light unit to irradiate light on the protection film;
a second light unit to irradiate light on a back surface of the display panel;
a pickup unit to capture a first image of the protection film in a state in which the pickup unit is coupled to the first light unit, and to capture a second image from the display panel and the protection film; and
a controller to receive the first and second images from the pickup unit, to compare the first image with the second image, and to determine whether a defect of the display panel is present.

15. An apparatus to inspect a display panel with a protection film, comprising:
a stage to position a display panel;
a light support unit including a light unit to irradiate light on the display panel;
a backlight unit installed at a back portion of the stage to irradiate light to the display panel;
a camera support including a camera installed thereon to capture a first image of the display panel when the camera is coupled to the light unit, and to capture a second image of the display panel when the camera is coupled to the backlight unit; and
a controller to receive first and second image signals corresponding to the first and second images, respectively, from the camera, and to determine whether the display panel contains a defect from a comparison of the two received images.

16. The apparatus according to claim 15, wherein the light support unit includes:
a first elevating rail arranged in a vertical direction;
a first elevating member coupled to the first elevating rail to enable a vertical moving operation;
a fixing lever installed on the first elevating member to fix the first elevating member; and
a horizontal moving rail provided at a side of the first elevating member; and
a horizontal moving slider installed on the horizontal moving rail and couple to an upper surface of the light unit to hold the same.

17. The apparatus according to claim 16, wherein the camera support includes:
a second elevating rail and a second elevating member coupled to the second elevating rail to enable a vertical moving operation of the camera.

18. The apparatus according to claim 15, wherein the stage is made of a material that transmits light irradiated to a back portion thereof from the backlight.

19. The apparatus of claim 15, further comprising:
an image processor to process the first and second image signals from the camera, and to recover a plurality of images from the processed image signals; and
a second controller to compare the images based on the image signals processed by the image processor, and to determine the presence of a defect of the display panel.

20. An apparatus to inspect a display panel, comprising:
an image capturing unit to capture first and second images of the display panel according to a pattern applied to the display panel;
a controller to determine whether the display panel has a defect, according to the first and second images; and
a light unit including a light emitting unit and a backlight to generate first and second lights, respectively,
wherein the controller determines whether the display panel has the defect, according to the first and second images captured when the first and second lights are radiated on the display panel, respectively.

21. The apparatus according to claim 20, wherein the first image does not detect a defect image of the display panel itself, and the second image detects the defect image of the display itself.

22. An apparatus to inspect a display panel, comprising:
an image capturing unit to capture a first image of the display panel at a first time and a second image of the display panel at a second time;
a pattern generator to apply a pattern to the display panel during at least one of the first time and the second time; and
a controller to compare the captured first and second images to determine whether any defects are present in the display panel, and if any defects are present in the display panel, the controller determines whether the defects are defects external to the display panel or defects that are internal to the display panel.

* * * * *